United States Patent
Fisk (10) Patent No.: US 10,791,945 B2
(45) Date of Patent: Oct. 6, 2020

(54) BIOCOMPATIBLE IMPLANTABLE ELECTRODE

(71) Applicant: Pulse Technologies, Inc., Quakertown, PA (US)

(72) Inventor: Andrew E. Fisk, Philadelphia, PA (US)

(73) Assignee: PULSE IP, LLC, Quakertown, PA (US)

( * ) Notice: Subject to any disclaimer, the term of this patent is extended or adjusted under 35 U.S.C. 154(b) by 905 days.

(21) Appl. No.: 13/905,851

(22) Filed: May 30, 2013

(65) Prior Publication Data

US 2014/0357973 A1    Dec. 4, 2014

(51) Int. Cl.
| | |
|---|---|
| *C25D 5/02* | (2006.01) |
| *A61B 5/04* | (2006.01) |
| *A61N 1/05* | (2006.01) |
| *A61B 5/042* | (2006.01) |
| *B23K 26/36* | (2014.01) |
| *B23K 26/352* | (2014.01) |
| *B23K 26/0622* | (2014.01) |

(52) U.S. Cl.
CPC ............... *A61B 5/04* (2013.01); *A61B 5/042* (2013.01); *A61N 1/05* (2013.01); *B23K 26/36* (2013.01); *C25D 5/02* (2013.01); *B23K 26/0624* (2015.10); *B23K 26/3584* (2018.08)

(58) Field of Classification Search
CPC ....................................................... A61N 1/05
See application file for complete search history.

(56) References Cited

U.S. PATENT DOCUMENTS

| | | | |
|---|---|---|---|
| 5,318,572 | A | 6/1994 | Helland et al. |
| 5,571,158 | A | 11/1996 | Bolz et al. |
| 6,799,076 | B2 | 9/2004 | Gelb et al. |
| 2007/0225785 | A1 | 9/2007 | Park et al. |
| 2007/0292667 | A1 | 12/2007 | Laude et al. |
| 2008/0183260 | A1 | 7/2008 | Nygren |
| 2008/0299289 | A1 | 12/2008 | Fisk |

(Continued)

FOREIGN PATENT DOCUMENTS

| | | |
|---|---|---|
| EP | 2808053 A1 | 12/2014 |
| WO | WO2007095549 A2 | 8/2007 |

OTHER PUBLICATIONS

Vorobyev et al. "Effect of surface structural modifications of platinum in multi-pulse femtosecond laser ablation" LFNM 2006.*

(Continued)

*Primary Examiner* — Luther Behringer
(74) *Attorney, Agent, or Firm* — Massina Pat. & TM Law, PLLC (57) ABSTRACT

A biocompatible, implantable electrode for electrically active medical devices. The implantable medical electrode has a surface geometry which optimizes the electrical performance of the electrode, while mitigating the undesirable effects associated with prior art porous surfaces. The electrode has an optimized surface topography for improved electrical performance. Such a electrode is suitable for devices which may be permanently implanted in the human body as stimulation electrodes, such as pacemakers, or as sensors of medical conditions. Such is achieved by the application of ultrafast high energy pulses to the surface of a solid, monolithic electrode material for the purpose of increasing the surface area and thereby decreasing its afterpotential polarization.

21 Claims, 5 Drawing Sheets

(56) References Cited

U.S. PATENT DOCUMENTS

| | | |
|---|---|---|
| 2011/0126410 A1 | 6/2011 | Capcelea et al. |
| 2011/0160821 A1 | 6/2011 | Jackson et al. |
| 2013/0085557 A1 | 4/2013 | Terasawa |
| 2013/0296678 A1* | 11/2013 | Larsen .................... A61N 1/05 600/373 |

OTHER PUBLICATIONS

Vorobyev, A.Y., and Chunlei Guo, "Femtosecond Laser Nanostructuring Ofmetals." Optics Press, vol. 14, No. 6; Mar. 20, 2006; pp. 2164-2169.

* cited by examiner

BIOCOMPATIBLE IMPLANTABLE ELECTRODE

BACKGROUND OF THE INVENTION

Field of the Invention

The present invention relates to a biocompatible, implantable electrode for electrically active medical devices. The electrode has an optimized surface topography for improved electrical performance. Such a electrode is suitable for devices which may be permanently implanted in the human body as stimulation electrodes, such as pacemakers, or as sensors of medical conditions. Such is achieved by the application of ultrafast high energy pulses to the surface of a solid, monolithic electrode material for the purpose of increasing the surface area and thereby decreasing its after-potential polarization.

Description of the Related Art

There is great commercial interest in producing active implantable devices which are typically electrodes used for the stimulation of tissue or the sensing of electrical biorhythms. The electrical performance of implantable electrodes can be enhanced by increasing the external surface area which is in contact with tissues inside the body. It is known that increasing the surface area of an implantable electrode increases the double layer capacitance of the electrode and reduces the after-potential polarization, thereby increasing device battery life, or allowing for lower capture thresholds, and improved sensing of certain electrical signals, such as R and P waves. It is known in the art to apply a coating to increase the surface area of the electrode thereby reducing the after-potential polarization. A reduction in after-potential polarization results in an increase in charge transfer efficiency by allowing increased charge transfer at lower voltages. This is of particular interest in neurological stimulation. Double layer capacitance is typically measured by means of electrochemical impedance spectroscopy. In this method an electrode is submerged in a electrolytic bath and a small cyclic wave is imposed on the electrode. The current and voltage response of the electrode/electrolyte system is measured to determine the double layer capacitance. The capacitance is the predominant factor in the impedance at low frequencies (<10 Hz) and thus the capacitance is typically measured at frequencies of 0.001 Hz-1 Hz.

The current state of the art for increasing the surface area of an implantable electrode is to apply a suitable coating to the surface of electrode substrates. A principal concern in any coating application is the joining of the substrate and coating material and the adhesion between them. In this regard, U.S. Pat. No. 5,571,158 shows a stimulation electrode having a porous surface coating whose active surface area is essentially larger than the surface area defined by the geometrical basic shape of the electrode. U.S. Pat. No. 6,799,076 discloses an electrode having a substrate with a first layer covering at least a portion of the substrate, and a second layer covering at least a portion of the first layer. The first layer consists of a carbide, nitride or carbonitride of titanium, vanadium, zirconium, niobium, molybdenum, hafnium, tantalum or tungsten. The second layer includes iridium. U.S. Pat. No. 5,318,572 teaches a high efficiency tissue stimulating and signal sensing electrode. A lead has a porous electrode of platinum-iridium with recessed areas or grooves formed into the surface. The grooves allow for acute electrode stabilization as a result of clot formation and endocardial tissue capture. At least one layer of a porous coating of 20-200 micron diameter spherical particles are deposited on the surface of the base electrode to obtain a porous macrostructure for promoting chronic tissue ingrowth. A microstructure surface coating is applied to increase the active surface area and enhance electrical efficiency by lowering electrochemical polarization and increasing electrical capacitance.

A particular concern for these techniques is that a section of coating might become dislodged in use and become an irritant. Current techniques for testing the adhesion of a coating to a substrate results in the destruction of the test piece which is costly and requires statistical evidence to validate the test method and sampling. A better alternative to a coating would be the modification of the electrode substrate material itself, thereby eliminating the issue of poor adhesion and the potential of coating particles becoming dislodged during use. Prior attempts to produce a suitable modified surface which does not include a coating have failed due to mechanical limitations. An example is found in U.S. patent publication 2011/0160821 where the surface is laser etched, thus producing ridges with features 25,000 nm to 250,000 nm. For a suitable electrode, the surface features need to be sub-millimeter, for example, from about 1 nm to about 1000 nm. Others have taught laser ablation of electrode surfaces, however, such techniques cannot achieve the nanometer scale feature size of this invention.

The present invention solves these issues by the application of ultra-fast energy pulses supplied to the surface. It has now been found that energy pulses delivered by means of an ultrafast laser produces surface structures on the order of 50 nm to 500 nm which is ideal for tissue stimulation. This process is produced not by laser etching and removal of material but by a restructuring of the surface. In the laser etching process of U.S. patent publication 2011/0160821 the surface is modified through the impingement of the laser, and the smallest feature that can be made equates to the size of the focused laser beam, which is limited by the wavelength of the laser, typically 200-1600 nm.

SUMMARY OF THE INVENTION

The invention provides an electrode comprising a solid, monolithic substrate having an outer peripheral surface; the outer peripheral surface having a topography defined by a plurality of voids distributed about the outer peripheral surface and extending a depth through the substrate; said voids having a depth through the substrate of from about 50 nm to about 500 nm; and said voids having a width of from about 50 nm to about 500 nm; said voids being spaced from adjacent voids a distance of from about 50 nm to about 250 nm.

The invention also provides a method for producing an electrode comprising a solid, monolithic substrate having an outer peripheral surface; the outer peripheral surface having a topography defined by a plurality of voids distributed about the outer peripheral surface and extending a depth through the substrate; said voids having a depth through the substrate of from about 50 nm to about 500 nm; and said voids having a width of from about 50 nm to about 500 nm; each void being spaced from adjacent voids a distance of from about 50 nm to about 250 nm, the method comprising exposing a solid, monolithic substrate to from about 10 to about 500 pulses of laser irradiation having a wavelength of from about 200 nm to about 1600 nm, at a pulse width of from about 1 femtosecond to about 5 picoseconds, and at a irradiance of from about 200 watts/cm$^2$ to about 5000 watts/cm$^2$.

DESCRIPTION OF THE INVENTION

Surface morphologies of implanted biomedical electrodes are designed to improve interaction with surrounding tissues. The invention provides biological benefits which exploit nanometer-scale features such as a reduced likelihood of infection, and functional benefits such as improved electrical transfer. The invention produces nanometer-scale features on biocompatible metals such as platinum by exposure to a femtosecond laser operating at various wavelengths. Laser induced surface structures produce an array of voids with length and depth ranging from about 50 nm to about 500 nm, depending on the laser parameters employed.

The invention realizes a performance advantage over typical prior art surface modifications by achieving an optimal surface geometry, which maximizes the effective surface area of the electrode while minimizing the after-potential polarization effect, thereby increasing charge transfer efficiency. After-potential polarization is the voltage remaining on an electrode after a stimulation pulse on the electrode from a device such as a pacemaker. It is a measure of how efficiently the charge is injected into the tissue.

It is known that the method for charge transfer in a medical electrode is by the charging and discharging of the electrical double layer capacitance formed on the surface of the electrode. This layer can be thought of as a simple parallel plate model in which the tissue to be stimulated is separated from the electrode surface by a barrier primarily of water, Na, K and Cl. The thickness of this layer is dictated by the concentration of the electrolyte in the body and is therefore uniform over the working life of the electrode. The thickness of an electrical double layer formed by an electrical conductor in 0.9% saline, i.e., body fluid is on the order of 1 nm and the expected thickness of the double layer capacitance formed in normal body electrolyte would be from about 0.5 nm to about 10 nm, more typically from about 5 to about 6 nm.

A typical human cell is on the order of from about 5,000 nm to about 10,000 nm in size. Because the cells are much larger than the layer and much smaller than the electrode surface, the cells can be thought of as being parallel to the surface of the electrode. As the non-polarized electrolyte (the electrolyte present but not participating in the electrical double layer) increases, the impedance of the tissue-electrode system increases. This is known as the solution resistance. The increased impedance results in a less effective charge transfer due to a dissipation of voltage along the solution resistance path. To minimize this impedance, the tissue to be stimulated should be as close to the electrode surface as possible. It would therefore be preferred, for these purposes, to have the electrode surface flat and placed parallel to the tissue.

The invention thus provides an electrode comprising a solid, monolithic substrate having an outer peripheral surface. The substrate comprises a biocompatible metal suitable for implanting within the tissues of a mammal. Examples non-exclusively include platinum, steel, alloys of platinum and iridium, alloys of nickel and cobalt, and combinations thereof. In one embodiment, the outer peripheral surface of an electrode has an area of from about 1 $mm^2$ to about 20 $mm^2$, preferably from about 3 $mm^2$ to about 12 $mm^2$. The electrode may have any suitable configuration or shape such as a tubular, flat, mushroom or corkscrew shape. The outer peripheral surface has a topography defined by a plurality of voids distributed about the outer peripheral surface and extending a depth through the substrate. The voids have a depth through the substrate of from about 50 nm to about 500 nm, preferably from about 100 nm to about 250 nm. The voids have a width of from about 50 nm to about 500 nm, preferably of from about 100 nm to about 250 nm. The voids are spaced from adjacent voids a distance of from about 50 nm to about 250 nm.

An electrode according to the invention, is produced by exposing an outer peripheral surface of a solid, monolithic substrate of such a biocompatible metal to pulses of laser irradiation. In one embodiment, a laser beam which produces a spot size of 100,000-800,000 nm is used to produce the structures. In one embodiment, the number of pulses of laser irradiation per spot ranges from about 10 to about 500 pulses, preferably from about 50 to about 400, and more preferably from about 100 to about 300. In one embodiment, the pulse wavelength is of from about 200 nm to about 1600 nm, preferably from about 400 to about 1,000, and more preferably from about 400 to about 800. In one embodiment, the pulse width ranges from about 1 femtosecond to about 5 picoseconds, preferably from about 100 femtoseconds to about 3 picoseconds, and at a irradiance of from about 200 watts/$cm^2$ to about 5000 watts/$cm^2$. Typically the laser irradiation produces a spot diameter of from about 10 μm to about 10,000 μm, preferably from about 25 μm to about 2,500 μm, and more preferably from about 50 μm to about 1,000 μm. Examples of suitable lasers non-exclusively include a Coherent Libra-F Ti:Sapphire amplifier laser system, and a Coherent AVIA laser. According to the invention, the resulting electrode has a polarization of about 1,000 mV or less, preferably about 500 mV or less, and more preferably about 200 mV or less. It has been determined that the lower the polarization of the electrode, the more optimized is the surface topography for improved electrical performance. The desirable characteristics of the surface, those being high double layer capacitance of the electrode and a low after-potential polarization effect, are enhanced when the surface area of the electrode is increased. A reduction in after-potential polarization results in an increase in charge transfer efficiency by allowing increased charge transfer at lower voltages. Thus a reduction of after-potential polarization increases device battery life, and improves sensing of certain electrical signals.

In use, the inventive electrode has at least one electrical connector electrically attached at an end thereof to the substrate. Typically, this may be a wire of a suitable material such as a biocompatible, conductive material such as platinum, silver, copper, a superalloy such as MP35N, or a material such as Nitrol. In one embodiment, the other end of the wire is connected to an electrical pulse generator such as a cardiac pacemaker.

In another embodiment, the other end of the wire is connected to an electrical measurement device such as a sensor of biological conditions, or a voltage recording device.

Figure 6:
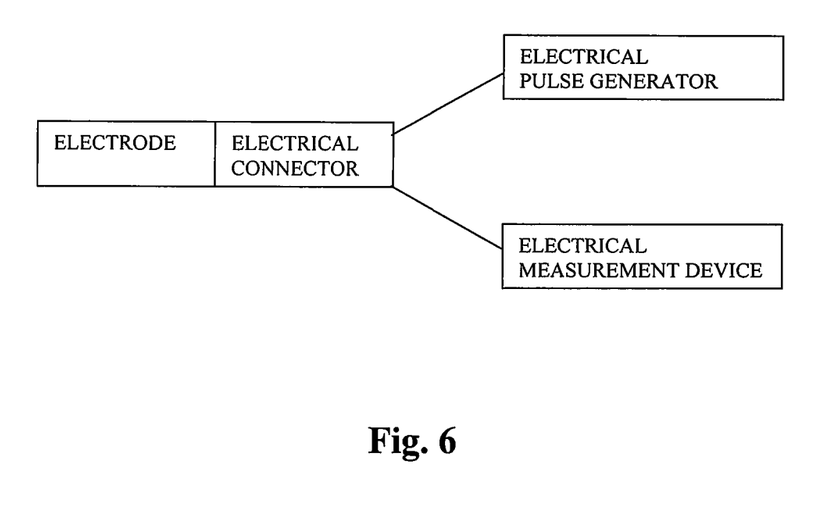
FIG. 6A illustrates an exemplary embodiment wherein the electrode is attached to an electrical connector and the electrical connector is attached to an electrical pulse generator.
FIG. 6B illustrates an exemplary embodiment wherein the electrode is attached to an electrical connector and the electrical connector is attached to an electrical measurement device.
Figure 6A:
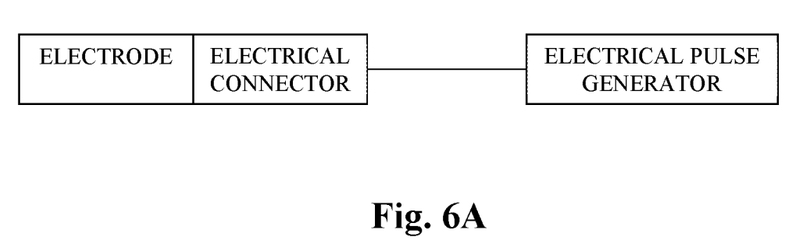
Figure 6B:
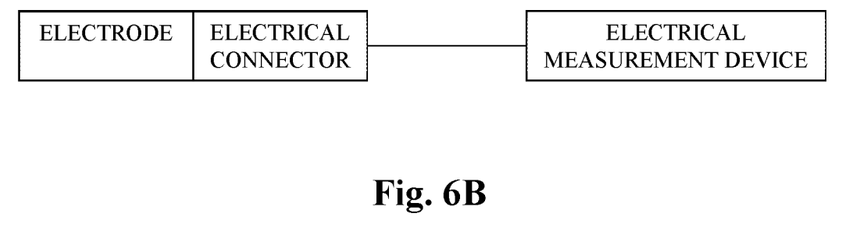

FIG. 6A illustrates an exemplary embodiment wherein the electrode is attached to an electrical connector and the electrical connector is attached to an electrical pulse generator. FIG. 6B illustrates an exemplary embodiment wherein the electrode is attached to an electrical connector and the electrical connector is attached to an electrical measurement device.

The following non-limiting examples serve to illustrate the invention.

EXAMPLES

A series of cylindrical platinum electrodes having a diameter of 2.2 mm and an active length of 0.75 mm was processed via ultrafast laser texturing. Each of the cylinders was rotated on its axis while the laser impinged the surface at a nearly oblique angle and the wavelength, number of pulses and laser irradiance were varied. Variations in operating parameters give the indicated potential polarization results. A Coherent Libra-F Ti:Sapphire amplifier laser system was used for the exposure.

Example 1

In this example, the laser exposure had a wavelength of 800 nm, an irradiance of 400 W/cm$^2$ and 100 pulses per spot. The resulting polarization was 600 mV. An example of a small surface feature size is approximately 4 nm and an example of a large surface feature size is approximately 107 nm.

Example 2

Figure 2:
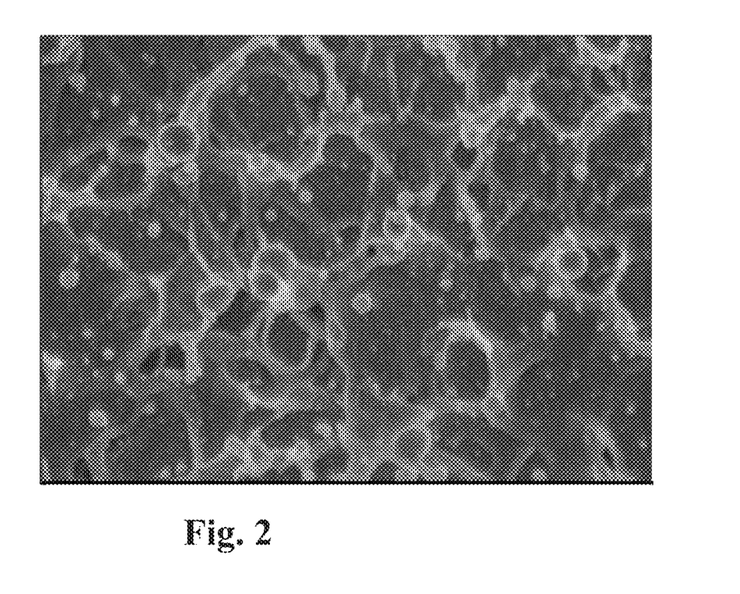
FIG. 2 illustrates the surface topography of an inventive electrode produced according to the conditions of Example 2.

In this example, the laser exposure had a wavelength of 800 nm, an irradiance of 400 W/cm$^2$ and 10 pulses per spot. The resulting polarization was 829 mV. The surface topography is shown in FIG. 2. The structure appears to be similar to that of Example 1, but the depth of the features is not as pronounced.

Example 3

Comparative

Figure 3:
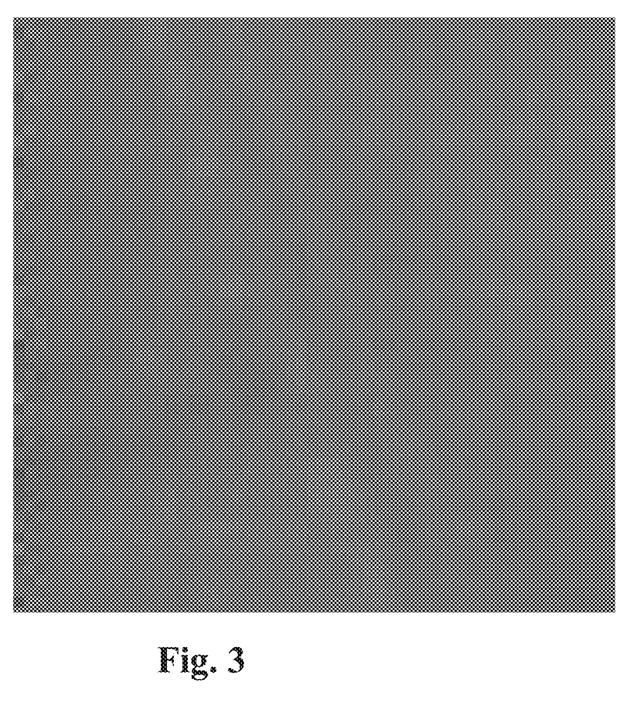
FIG. 3 illustrates the surface topography of an comparative electrode produced according to the conditions of Comparative Example 3.

In this example, the laser exposure had a wavelength of 800 nm, an irradiance of 100 W/cm$^2$ and 50 pulses per spot. The resulting polarization was 1100 mV, which is similar to that of an un-processed sample. FIG. 3 shows the desired inventive structure does not appear to be present.

Example 4

Figure 1:
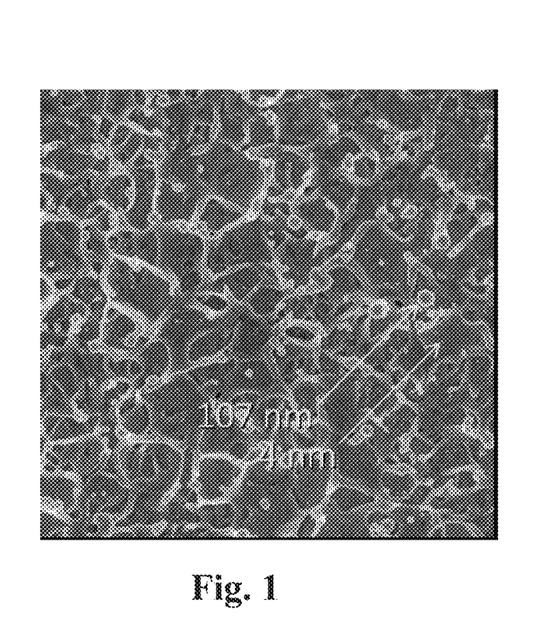
FIG. 1 illustrates the surface topography of an inventive electrode produced according to the conditions of Example 1.
Figure 4:
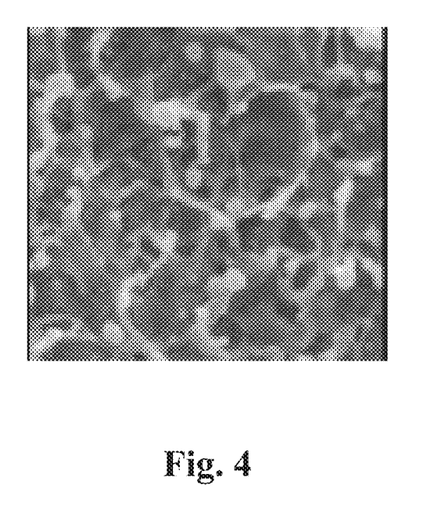
FIG. 4 illustrates the surface topography of an inventive electrode produced according to the conditions of Example 4.
Figure 5:
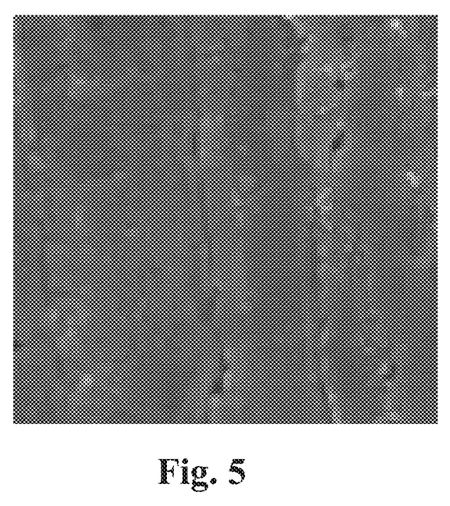
FIG. 5 illustrates the surface topography of an comparative electrode produced according to the conditions of Comparative Example 5.

In this example, the laser exposure had a wavelength of 400 nm, an irradiance of 1000 W/cm$^2$ and 100 pulses per spot. The resulting polarization was 700 mV. FIG. 4 shows the structure appears to be similar to FIG. 1 but with less definition in the features.

Example 5

Comparative

In this example, the laser exposure had a wavelength of 400 nm, an irradiance of 64 W/cm$^2$ and 10 pulses per spot. The resulting polarization was 996 mV. The surface does not present any features of the invention. The only features present are due to the process used to form the material into bar stock.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. An electrode comprising a solid, monolithic substrate having an outer peripheral surface; the outer peripheral surface having a topography defined by a plurality of voids distributed about the outer peripheral surface and extending a depth through the substrate; said voids having a depth through the substrate of from about 50 nm to about 500 nm; and said voids having a width of from about 50 nm to about 500 nm; said voids being spaced from adjacent voids a distance of from about 50 nm to about 250 nm.

2. The electrode of claim 1 wherein said voids having a depth through the substrate of from about 100 nm to about 250 nm; and said voids having a width of from about 100 nm to about 250 nm.

3. The electrode of claim 1 which has a configuration suitable for implanting within the tissues of a mammal.

4. The electrode of claim 1 wherein the substrate comprises a biocompatible metal.

5. The electrode of claim 1 wherein the substrate comprises platinum, steel, an alloy of platinum and iridium, an alloy of nickel and cobalt, or combinations thereof.

6. The electrode of claim 1 having an outer peripheral surface area of from about 1 mm$^2$ to about 20 mm$^2$.

7. The electrode of claim 1 further comprising at least one electrical connector electrically attached at an end thereof to the substrate.

8. The electrode of claim 7 further comprising an electrical pulse generator attached to another end of said electrical connector.

9. The electrode of claim 7 further comprising an electrical measurement device attached to another end of said electrical connector.

10. A method for producing an electrode comprising a solid, monolithic substrate having an outer peripheral surface; the outer peripheral surface having a topography defined by a plurality of voids distributed about the outer peripheral surface and extending a depth through the substrate; said voids having a depth through the substrate of from about 50 nm to about 500 nm; and said voids having a width of from about 50 nm to about 500 nm; each void being spaced from adjacent voids a distance of from about 50 nm to about 250 nm, the method comprising exposing a solid, monolithic substrate to from about 10 to about 500 pulses of laser irradiation having a wavelength of from about 200 nm to about 1600 nm, at a pulse width of from about 1 femtosecond to about 5 picoseconds, and at a irradiance of from about 200 watts/cm$^2$ to about 5000 watts/cm$^2$.

11. The method of claim 10 wherein the laser irradiation on the outer peripheral surface has a spot diameter of from about 10 μm to about 10,000 μm.

12. The method of claim 10 wherein said voids have a depth through the substrate of from about 100 nm to about 250 nm; and said voids having a width of from about 100 nm to about 250 nm.

13. The method of claim 10 wherein the electrode has a configuration suitable for implanting within the tissues of a mammal.

14. The method of claim 10 wherein the substrate comprises a biocompatible metal.

15. The method of claim 10 wherein the substrate comprises platinum, steel, an alloy of platinum and iridium, an alloy of nickel and cobalt, or combinations thereof.

16. The method of claim 10 wherein the electrode has an outer peripheral surface area of from about 1 mm$^2$ to about 20 mm$^2$.

17. The method of claim 10 further comprising electrically attaching at least one electrical connector at an end thereof to the substrate.

18. The method of claim 17 further comprising electrically attaching an electrical pulse generator to another end of said electrical connector.

19. The method of claim 17 further comprising electrically attaching an electrical measurement device to another end of said electrical connector.

20. A method which comprises implanting the electrode of claim 1 within the tissues of a mammal.

21. An electrode comprising a solid, monolithic substrate having an outer peripheral surface; the outer peripheral surface having at least an area defined by restructured surface material with a topography having a plurality of voids distributed about the outer peripheral surface and extending a depth through the substrate; said voids having a depth through the substrate of from about 50 nm to about 500 nm; and said voids having a width of from about 50 nm to about 500 nm; said voids being spaced from adjacent voids a distance of from about 50 nm to about 250 nm.

* * * * *